United States Patent [19]

Weissmüller et al.

[11] Patent Number: 4,826,836
[45] Date of Patent: May 2, 1989

[54] SACCHARINE SALTS OF AMINOMETHYL HETEROCYCLIC COMPOUNDS, COMPOSITIONS AND USE

[75] Inventors: Joachim Weissmüller, Monheim; Wolfgang Krämer, Burscheid; Paul Reinecke; Gerd Hänssler, both of Leverkusen, all of Fed. Rep. of Germany

[73] Assignee: Bayer Aktiengesellschaft, Leverkusen, Fed. Rep. of Germany

[21] Appl. No.: 118,143

[22] Filed: Nov. 5, 1987

[30] Foreign Application Priority Data

Nov. 22, 1986 [DE] Fed. Rep. of Germany ....... 3639903

[51] Int. Cl.$^4$ .................. A01N 43/80; A01N 43/84; C07D 413/14
[52] U.S. Cl. ................... 514/212; 514/227.5; 514/231.5; 514/253; 514/321; 514/373; 540/596; 544/60; 544/62; 544/135; 544/368; 546/198; 548/210; 548/211
[58] Field of Search .............. 540/596; 544/60, 62, 544/135, 368; 546/198; 548/210, 211; 514/212, 222, 229, 253, 321, 373, 231.5

[56] References Cited

U.S. PATENT DOCUMENTS 4,503,059 3/1985 Krämer et al. .................. 549/451

FOREIGN PATENT DOCUMENTS 3430805 9/1985 Fed. Rep. of Germany .

Primary Examiner—Robert W. Ramsuer
Attorney, Agent, or Firm—Sprung Horn Kramer & Woods

[57] ABSTRACT

Fungicidally active novel saccharine salts of aminomethyl heterocyclic compounds of the formula

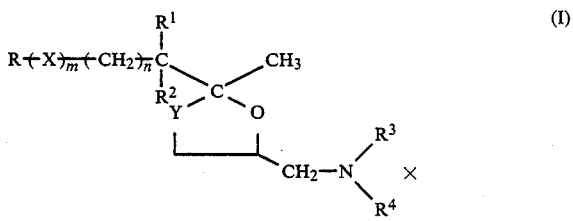

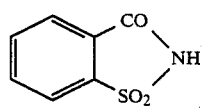

in which
R represents optionally substituted cycloalkyl, optionally substituted aryl or optionally substituted thienyl,
$R^1$ represents hydrogen or alkyl,
$R^2$ represents alkyl,
$R^3$ represents alkyl and
$R^4$ represents alkyl, alkenyl or alkinyl, or
$R^3$ and $R^4$, together with the nitrogen atom to which they are bonded, represent an optionally substituted saturated heterocyclic radical which can contain further hetero atoms,
X represents oxygen or sulphur,
Y represents oxygen, sulphur or the methylene group,
m represents 0 or 1 and
n represents 0 or 1.

21 Claims, No Drawings

SACCHARINE SALTS OF AMINOMETHYL HETEROCYCLIC COMPOUNDS, COMPOSITIONS AND USE

The invention relates to new saccharine salts of aminomethyl heterocyclic compounds, a process for their preparation and their use as agents for combating pests.

It is already known that saccharine salts of amino heterocyclic compounds, such as, for example, the saccharine salt of 5-amino-1,2,4-triazole, have fungicidal properties (compare European Pat. No. 158,074).

It is also known that certain aminomethyl heterocyclic compounds, such as, for example, 2-[1-(2-methylphenoxy)-2-methyl-prop-2-yl]-2-methyl-4-(piperidin-1-ylmethyl)-1,3-dioxolane, also have fungicidal properties (compare, for example, European Pat. No. 97,822).

However, their action is not completely satisfactory in all fields of use, especially when low amounts are applied and in the case of low concentrations.

New saccharine salts of aminomethyl heterocyclic compounds of the general formula (I)

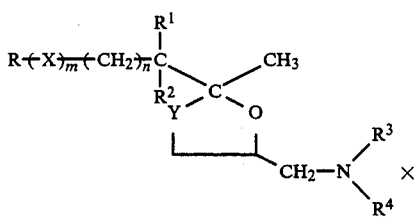

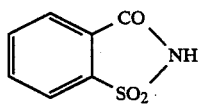

in which
R represents optionally substituted cycloalkyl, optionally substituted aryl or optionally substituted thienyl,
R¹ represents hydrogen or alkyl,
R² represents alkyl,
R³ represents alkyl and
R⁴ represents alkyl, alkenyl or alkinyl, or
R³ and R⁴, together with the nitrogen atom to which they are bonded, represent an optionally substituted saturated heterocyclic radical which can contain further hetero atoms,
X represents oxygen or sulphur,
Y represents oxygen, sulphur or the methylene group,
m represents 0 or 1 and
n represents 0 or 1,
have been found.

The compounds of the formula (I) can be in the form of geometric and/or optical isomers or isomer mixtures of varying composition. Both the pure isomers and the isomer mixtures are within the present invention.

It has furthermore been found that the new saccharine salts of aminomethyl heterocyclic compounds of the general formula (I)

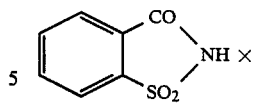

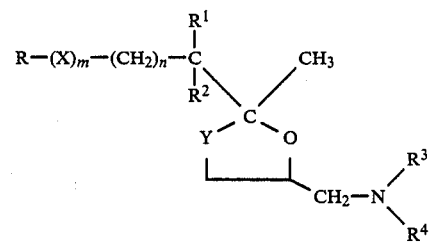

in which
R represents optionally substituted cycloalkyl, optionally substituted aryl or optionally substituted thienyl,
R¹ represents hydrogen or alkyl,
R² represents alkyl,
R³ represents alkyl and
R⁴ represents alkyl, alkenyl or alkinyl, or
R³ and R⁴, together with the nitrogen atom to which they are bonded, represent an optionally substituted saturated heterocyclic radical which can contain further hetero atoms,
X represents oxygen or sulphur,
Y represents oxygen, sulphur or the methylene group,
m represents 0 or 1 and
n represents 0 or 1,
are obtained by a process in which aminomethyl heterocyclic compounds of the formula (II)

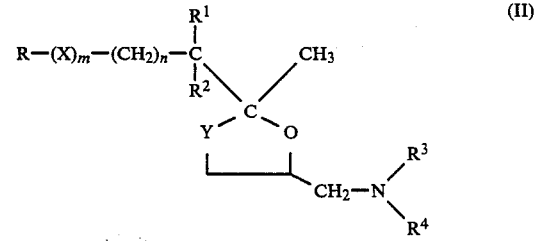

in which
R, R¹, R², R³, R⁴, X, Y, m and n have the abovementioned meaning,
are reacted with saccharine, if appropriate in the presence of a diluent.

Finally, it has been found that the new saccharine salts of aminomethyl heterocyclic compounds of the general formula (I) have an action against pests.

Surprisingly, the new saccharine salts of aminomethyl heterocyclic compounds of the general formula (I) inter alia have a better fungicidal activity than the saccharine salts of amino heterocyclic compounds which are known from the prior art, such as, for example, the saccharine salt of 5-amino-1,2,4-triazoles, these being closely related compounds chemically and from the point of view of their action.

Formula (I) provides a general definition of the saccharine salts, according to the invention, of aminomethyl heterocyclic compounds. Preferred salts of the formula (I) are those in which R represents phenyl or thienyl which is optionally mono-, di-, tri-, tetra- or pentasubstituted by identical or different substituents, possible substituents being: halogen and in each case straight-chain or branched alkyl, alkoxy, alkylthio, halogenoalkyl, halogenoalkoxy and halogenoalkylthio with in each case 1 to 4 carbon atoms and if appropriate 1 to 9 identical or different halogen atoms; or represents cycloalkyl which has 3 to 7 carbon atoms and is optionally monosubstituted or polysubstituted by identical or different lower alkyl groups, $R^2$ represents hydrogen, or represents straight-chain or branched alkyl with 1 to 4 carbon atoms, $R^2$ represents straight-chain or branched alkyl with 1 to 4 carbon atoms, $R^3$ represents straight-chain or branched alkyl with 1 to 6 carbon atoms and $R^4$ represents in each case straight-chain or branched alkyl, alkenyl or alkinyl with in each case up to 8 carbon atoms, or $R^3$ and $R^4$, together with the nitrogen atom to which they are bonded, represent a heterocyclic radical which has 5 to 7 ring members 1 or 2 hetero atoms and is optionally monosubstituted or polysubstituted by identical or different substitents, possible hetero atoms being nitrogen and oxygen and possible substituents being: straight-chain or branched alkyl with 1 to 4 carbon atoms, hydroxymethyl and derivatives thereof, such as ethers and esters, and straight-chain or branched alkoxycarbonyl with 1 to 4 carbon atoms, X represents oxygen or sulphur, Y represents oxygen, sulphur or the methylene group, m represents 0 or 1 and n represents 0 or 1.

Particularly preferred salts of the formula (I) are those in which

R represents phenyl which is optionally mono-, di- or trisubstituted by identical or different substituents, possible substituents being: fluorine, chlorine, bromine, methyl, ethyl, n- and i-propyl, n-, i-, s- and t-butyl, methoxy, ethoxy, n- and i-propoxy, methylthio, trifluoromethyl, trifluoromethoxy and trifluoromethylthio; or represents cyclohexyl which is optionally mono-, di-, tri-, tetra- or pentasubstituted by identical or different substituents, possible substituents being: methyl, ethyl, n- and i-propyl and n-, i-, s- and t-butyl; or represents thienyl which is optionally mono- or disubstituted by identical or different substituents, possible substituents being: fluorine, chlorine, bromine, methyl, ethyl, n- or i-propyl and n-, i-, s- or t-butyl, $R^1$ represents hydrogen or methyl, $R^2$ represents methyl or ethyl, $R^3$ represents methyl and $R^4$ represents methyl, ethyl, n- or i-propyl, n- or i-butyl, n- or i-pentyl, n- or i-hexyl, allyl, butenyl, n- or i-pentenyl, n- or i-hexenyl, proparyl, butinyl, n- or i-pentinyl or n- or i-hexinyl or $R^3$ and $R^4$, together with the nitrogen atom to which they are bonded, represent a heterocyclic radical of the formula

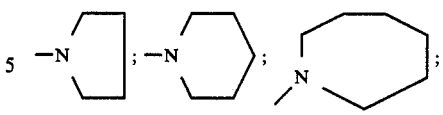

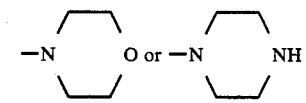

which is optionally mono-, di-, tri- or tetrasubstituted by identical or different substituents, possible substituents being: metyl, ethyl, phenyl, hydroxymethyl, methoxymethyl, ethoxymethyl, acyloxymethyl, methoxycarbonyl or ethoxycarbonyl, X represents oxygen and sulphur, Y represents oxygen, sulphur or the methylene group, m represents 0 or 1 and n represents 0 or 1.

The following saccharine salts of the general formula (I) may be mentioned specifically, in addition to the compounds mentioned in the preparation examples:

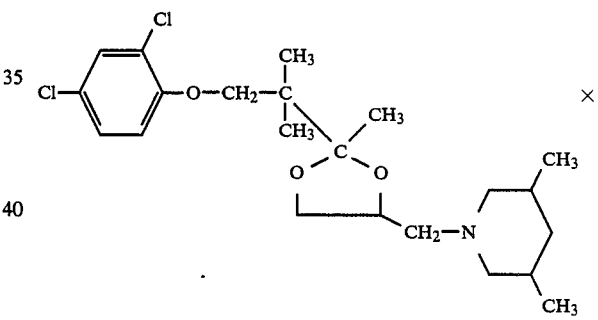

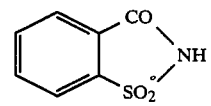

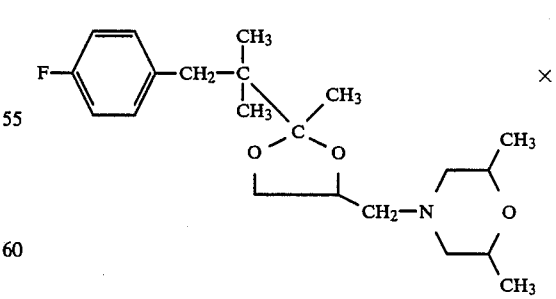

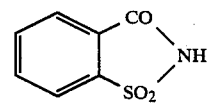

-continued

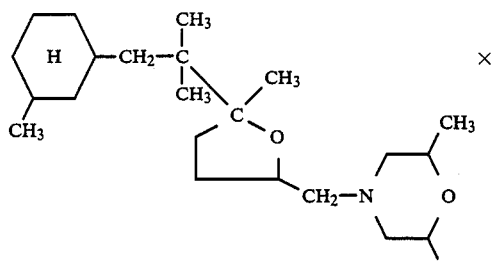

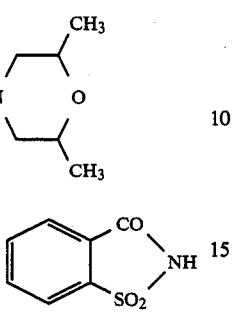

×

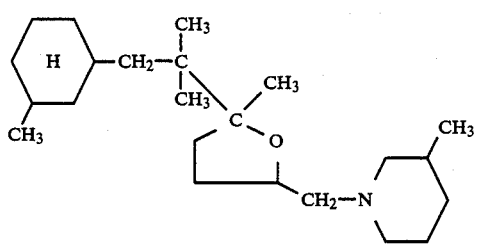

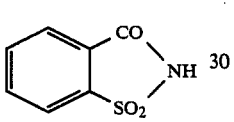

×

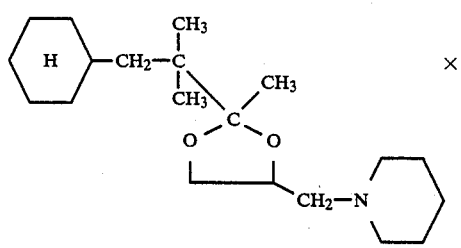

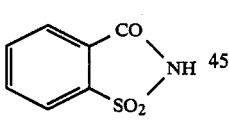

×

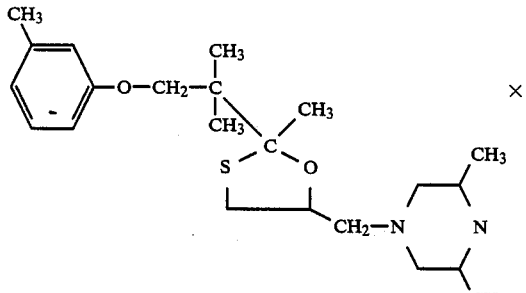

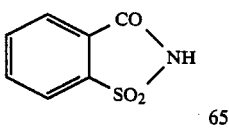

×

If, for example, 2-[1-(3-chlorophenoxy)-2-methyl-prop-2-yl]-2-methyl-4-[(2,6-dimethyl-4-morpholinyl)-methyl]-1,3-dioxolane and saccharine are used as start- ing substances, the course of the reaction in the process according to the invention can be represented by the following equation:

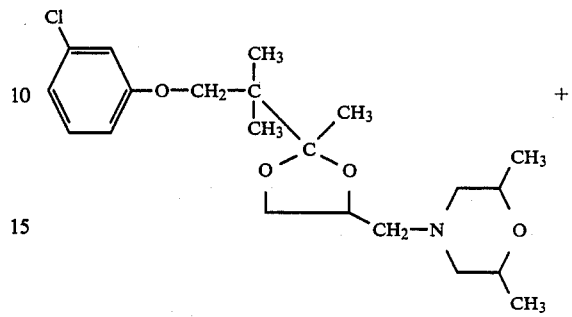 +

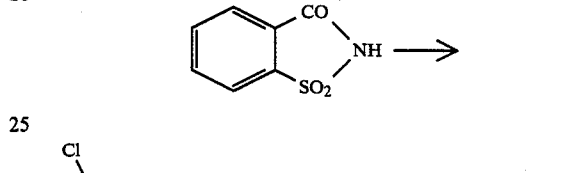 →

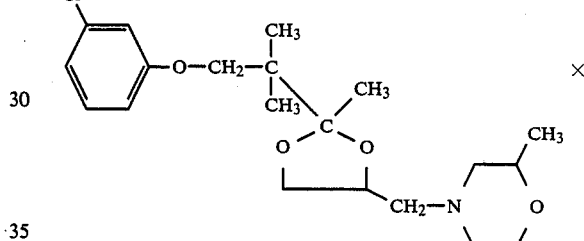

Formula (II) provides a general definition of the aminomethyl heterocyclic compounds required as starting substances for carrying out the process according to the invention. In this formula (II), R, $R^1$, $R^2$, $R^3$, $R^4$, X, Y, m and n represent those radicals which have already been mentioned for these substituents in connection with the description of the substances of the formula (I).

The aminomethyl heterocyclic compounds of the formula (II) are known in most cases or can be obtained with the aid of known processes by analogous methods (compare, for example, European Pat. No. 97,822; DE-OS (German Published Specification) No. 3,413,996; DE-OS (German Published Specification) No. 3,324,769; and DE-OS (German Published Specification) No. 3,328,151).

They are obtained, for example, by a process in which substituted heterocyclic compounds of the formula (III)

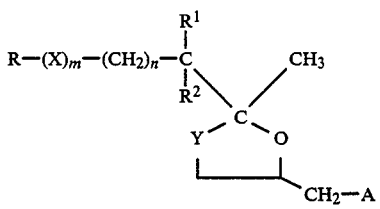

in which
- R, $R^1$, $R^2$, X, Y, m and n have the abovementioned meaning and
- A represents an electron-withdrawing leaving group, in particular chlorine or bromine, methanesulphonyloxy or p-toluenesulphonyloxy, are reacted with amines of the formula (IV)

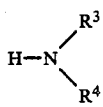

in which
- $R^3$ and $R^4$ have the abovementioned meaning, if appropriate in the presence of a diluent, such as, for example, ethanol, if appropriate in the presence of an acid-binding agent, such as, for example, potassium carbonate, and if appropriate in the presence of a catalyst, such as, for example, potassium iodide, at temperatures between 50° C. and 250° C.

The substituted heterocyclic compounds of the formula (III) are known in most cases (compare, for example, European Pat. No. 97,822; DE-OS (German Published Specification) No. 3,413,966, DE-OS (German Published Specification) No. 3,324,760; and DE-OS (German Published Specification) No. 3,328,155), or they are obtainable analogously to known processes (compare also the preparation examples).

The amines of the formula (IV) are generally known compounds of organic chemistry.

Possible diluents for carrying out the process according to the invention are inert organic solvents.

These include, in particular, ethers, such as ethylene glycol dimethyl or diethyl ether; ketones, such as acetone or butanone; nitriles, such as acetonitrile or propionitrile; amides, such as dimethylformamide, dimethylacetamide, N-methylformanilide, N-methylpyrrolidone or hexamethylphosphoric acid triamide, or alcohols, such as methanol, ethanol or propanol.

The reaction temperatures can be varied within a substantial range in carrying out the process according to the invention. The reaction is in general carried out at temperatures between 0° C. and 100° C., preferably at temperatures between 10° C. and 50° C.

For carrying out the process according to the invention, equimolar amounts of saccharine are employed per mol of aminomethyl heterocyclic compound of the formula (II). The two reaction partners are dissolved in a suitable solvent at the suitable reaction temperature and the solvent is then removed by distillation in vacuo. The salts thus obtainable are purified with the aid of customary purification methods, for example by recrystallization or reprecipitation. The salts, which are occasionally amorphos, are characterized with the aid of spectroscopic methods (IR; NMR).

The active compounds according to the invention have a powerful action against pests and can be used in practice for combating undesirable harmful organisms. The active compounds are particularly suitable for use as plant protection agents, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal and bacterial diseases which come under the generic names listed above may be mentioned as examples, but not by way of limitation: Pythium species, such as, for example, *Phythium ultimum;* Phytophthora species, such as, for example, *Phytophthora infestans;* Pseudoperonospora species, such as, for example, *Pseudoperonospora humuli* or *Pseudoperonospora cubensis;* Plasmopara species, such as, for example, *Plasmopara viticola;* Peronospora species, such as, for example, *Peronospora pisi* or *P. brassicae;* Erysiphe species, such as, for example, *Erysiphe graminis;* Sphaerotheca species, such as, for example, *Sphaerotheca fuliginea;* Podosphaera species, such as, for example, *Podosphaera leucotricha;* Venturia species, such as, for example, *Venturia inaequalis;* Pyrenophora species, such as, for example, *Pyrenophora teres* or *P. graminea* (conidia form: Drechslera, syn: Helminthosporium); Cochliobolus species, such as, for example, *Cochliobolus sativus* (conidia form: Drechslera, syn: Helminthosporium); Uromyces species, such as, for example, *Uromyces appendiculatus;* Puccinia species, such as, for example, *Puccinia recondita; Tilletia species,* such as, for example, Tilletia caries; Ustilago species, such as, for example, *Ustilago nuda* or *Ustilago avenae;* Pellicularia species, such as, for example, *Pellicularia sasakii;* Pyricularia species, such as, for example, *Pyricularia oryzae;* Fusarium species, such as, for example, *Fusarium culmorum;* Botrytis species, such as, for example, Botrytis cinerea; Septoria species, such as, for example, *Septoria nodorum;* Leptosphaeria species, such as, for example, *Leptosphaeria nodorum;* Cercospora species, such as, for example, *Cercospora canescens;* Alternaria species, such as, for example, *Alternaria brassicae* and Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

The active compounds according to the invention can thereby be used with particularly good success for combating cereal diseases, such as, for example, against the powdery mildew of cereals causative organism (*Erysiphe graminis*), against the leaf spot disease causative organism (*Pyrenophora teres*), against Puccinia species and Septoria species and against the rice spot disease causative organism (*PYricularia oryzae*). It should be emphasized that as well as having a good protective activity, the active compounds according to the invention also have systemic properties.

Depending on their particular physical and/or chemical properties, the active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and furthermore in formulations used in burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefield gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of orgaic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active copounds according to the invention can be present in the formulations as a mixture with other known active compounds, such as fungicides, insecticides, acaricides and herbicides, and in mixtures with fertilizers and growth regulators.

The active compounds can be used as such or in the form of their formulations or the use forms prepared therefrom, such as ready-to-use solutions, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seed of the plants can also be treated.

In the treatment of parts of plants, the active compound concentrations in the use forms can be varied within a substantial range. They are, in general, between 1 and 0.0001% by weight, preferably between 0.5 and 0.0001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

PREPARATION EXAMPLES

EXAMPLE 1

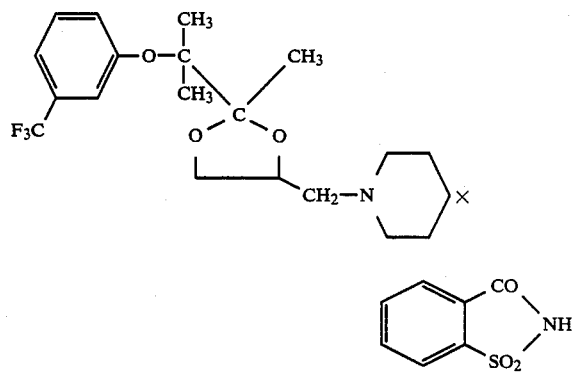

4.85 g (0.012 mol) of 2-[2-(3-trifluoromethylphenoxy)-prop-2-yl]-2-methyl-4-(piperidin-1-yl-methyl)-1,3-dioxolane are dissolved in 50 ml of ethanol together with 2.17 g (0.012 mol) of saccharine. The clear solution is evaporated in vacuo and the residue is dried under a high vacuum. 7 g (100% of theory) of 2-[2-(3-trifluoromethyl-phenoxy)-prop-2-yl]-2-methyl-4-(piperidin-1-yl-methyl)-1,3-dioxolane saccharine salt are obtained as an amorphous compound.

NMR (CDCl$_3$/TMS): δ=4.4–4.6 (m, 1H); 4.2–4.35 (m, 1H), 3.5–3.7 (m, 3H) ppm.

PREPARATION OF THE STARTING COMPOUNDS OF THE FORMULA (II)

1(a)

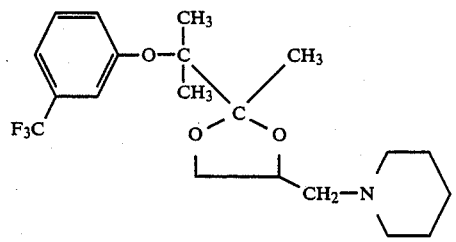

8.4 g (0.025 mol) of 2-[2-(3-trifluoromethylphenoxy)-prop-2-yl]-2-methyl-4-chloromethyl-1,3-dioxolane are stirred together with 10 g (0.11 mole) of piperidine at a bath temperature of 140° C. for 14 hours. For working up, the cooled reaction mixture is taken up in ether, washed several times with water, dried over sodium sulphate and concentrated in vacuo and the residue is distilled under a high vacuum.

9.3 g (96% of theory) of 2-[2-(3-trifluoromethyl-phenoxy)-prop-2-yl]-2-methyl-4-(piperidin-1-yl-methyl)-1,3-dioxolane of refractive index $n_D^{20}$ 1.4711 are obtained.

PREPARATION OF THE PRECURSORS OF THE FORMULA (III)

1(b)

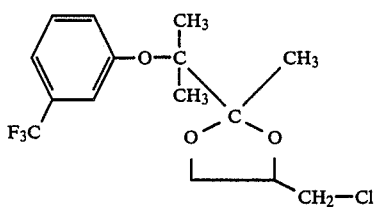

12.3 g (0.5 mol) of 3-(3-trifluoromethyl-phenoxy)-3-methyl-butan-2-one are heated under reflux together with 110 g (1 mol) of 3-chloropropanediol and 10 g of acid ion exchanger (Lewasorb A10) in 600 ml of toluene over a water separator for 14 hours. The cooled reaction mixture is filtered and the filtrate is dried over sodium sulphate and concentrated. The residue is distilled under a high vacuum. 109 g (65% of theory) of 2-[2-(3-trifluoromethyl-phenoxy)-prop-2-yl]-2-methyl-4-chloromethyl-1,3-dioxolane of boiling point 163° C. under 0.2 mbar are obtained.

PREPARATION OF PRECURSORS FOR THE PREPARATION OF COMPOUNDS OF THE FORMULA (III)

1(c)

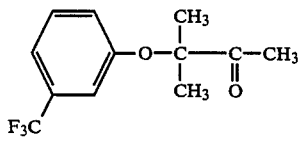

130 g (0.75 mol) of 2-bromo-2-methyl-butan-3-one are added dropwise to a mixture of 121 g (0.75 mol) of 3-trifluoromethylphenol, 110 g (0.75 mol) of potassium carbonate and 1.5 g of tetrabutylammonium bromide in 500 ml of butanone at 60° C., with stirring, and when the addition has ended the mixture is stirred at 80° C. for 16 hours. For working up, the cooled reaction mixture is filtered, the filtrate is concentrated in vacuo and the residue is distilled under a high vacuum.

137 g (74% of theory) of 3-(3-trifluoromethylphenoxy)-3-methyl-butan-2-one of boiling point 60° C.–62° C. under 0.5 mbar are obtained.

EXAMPLE 2

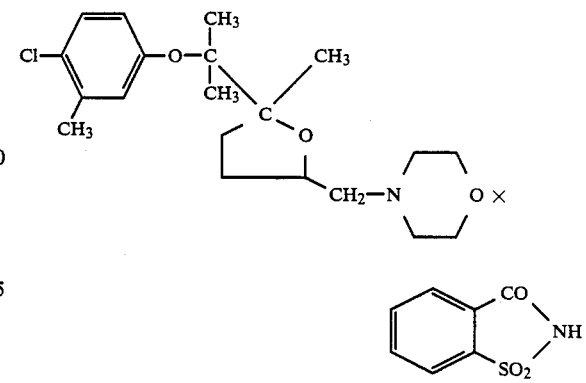

1.8 g (0.01 mol) of saccharine are added to 3.6 g (0.01 mol) of 2-[2-(4-chloro-3-methylphenoxy)-prop-2-yl]-2-methyl-5-(4-morpholinylmethyl)-tetrahydrofuran in 50 ml of acetone. The clear solution is evaporated in vacuo and the residue is dried under a high vacuum.

5.4 g (100% of theory) of 2-[2-(4-chloro-3-methyl-phenoxy)-prop-2-yl]-2-methyl-5-(4-morpholinyl-methyl)-tetrahydrofuran saccharine salt are obtained as an amorphous compound.

1H-NMR (CDCl$_3$/TMS): δ=4.45–4.7 (m, 1H); 4.07 (m, 3H) ppm.

PREPARATION OF THE STARTING COMPOUND OF THE FORMULA (II)

2(a)

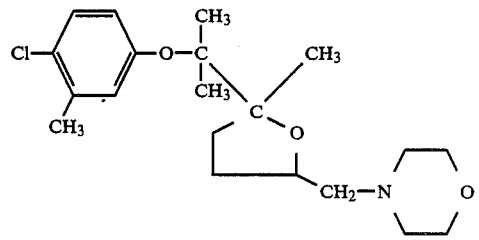

18.5 g (0.05 mol) of 2-bromomethyl-5-[2-(4-chloro-3-methyl-phenoxy)-prop-2-yl]-5-methyl-tetrahydrofuran are stirred together with 14 g (0.16 mol) of morpholine at a bath temperature of 130° C. for 13 hours. For working up, the cooled reaction mixture is taken up in ether, washed several times with water, dried over sodium sulphate and concentrated in vacuo and the residue is purified by chromatography (silica gel; mobile phase: petroleum ether/ethyl acetate 1:1).

12.7 g (68% of theory) of 2-[2-(4-chloro-3-methyl-phenoxy)-prop-2-yl]-2-methyl-5-(4-morpholinylmethyl)-tetrahydrofuran of refractive index $n_D^{20}$ 1.5139 are obtained.

PREPARATION OF THE PRECURSOR OF THE FORMULA (III)

2(b)

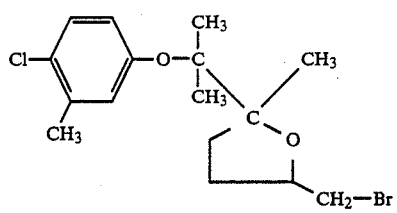

60 g (0.37 mol) of N-bromosuccinimide are added in portions to 88.8 g (0.3 mol) of 6-(4-chloro-3-methylphenoxy)-5-hydroxy-5,6,6-trimethyl-1-hexene in 600 ml of absolute chloroform, while stirring and cooling, so that the reaction temperature does not exceed 40° C. When the addition has ended, the mixture is stirred at room temperature for a further 14 hours and then washed twice with water and dried over sodium sulphate and the solvent is removed in vacuo. 94 g (82% of theory) of 2-bromomethyl-5-[2-(4-chloro-3-methylphenoxy)-prop-2-yl]-5-methyl-tetrahydrofuran are obtained and are further reacted without purification.

PREPARATION OF THE PRECURSOR OF COMPOUNDS OF THE FORMULA (III)

2(c)

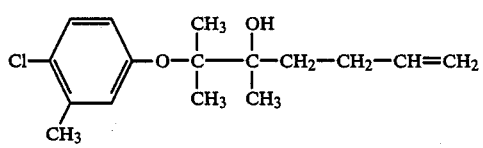

101 g (0.42 mol) of 2-[2-(4-chloro-3-methylphenoxy)-prop-2-yl]-2-methyl-oxirane are added dropwise to a solution of 10 g (0.4 mol) of magnesium and 48 g (0.4 mol) of allyl bromide in 400 ml of absolute ether, while stirring and cooling. When the addition has ended, the mixture is warmed at the boiling point for 4 hours and aqueous ammonium chloride solution is then carefully added to the cooled reaction mixture until no further evolution of gas occurs. The organic phase is separated off, dried over sodium sulphate and concentrated in vacuo and the residue is distilled under a high vacuum. 97 g (86% of theory) of 6-(4-chloro-3-methylphenoxy)-5-hydroxy-5,6,6-trimethyl-1-hexene of boiling point 118° C.–120° C. under 0.01 mbar are obtained.

PREPARATION OF THE PRECURSOR 2C

2(d)

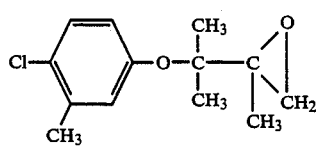

23 g (0.42 mol) of sodium methylate are added to a suspension of 100 g (0.45 mol) of trimethylsulphoxonium iodide in 100 g of dimethyl sulphoxide in the course of 10 minutes, the mixture is then diluted with 200 ml of absolute tetrahydrofuran and stirred at room temperature for 3 hours, 104 g (0.46 mol) of 2-(4-chloro-3-methyl-phenoxy)-2-methyl-butan-3-one are subsequently added and the mixture is stirred at room temperature for 32 hours. The solid which has precipitated is filtered off, the filtrate is concentrated in vacuo, the residue is taken up in methylene chloride and the mixture is washed with water, dried over sodium sulphate and freed from the solvent in vacuo.

86.7 g (85% of theory) of 2-[2-(4-chloro-3-methylphenoxy)-prop-2-yl]-2-methyl-oxirane are obtained as an oil which is further reacted without purification.

PREPARATION OF THE PRECURSOR OF 2D

2(e)

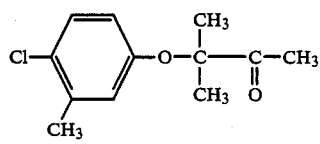

130 g (0.75 mol) of 2-bromo-2-methyl-butan-3-one are added dropwise to a mixture of 107 g (0.75 mol) of 4-chloro-3-methylphenol, 110 g of potassium carbonate and 1.5 g of tetrabutylammonium bromide in 500 ml of butanone at 60° C., with stirring, and after the addition has ended the mixture is stirred at 80° C. for 16 hours. For working up, the cooled reaction mixture is filtered, the filtrate is concentrated in vacuo and the residue is distilled under a high vacuum.

110 g (65% of theory) of 2-(4-chloro-3-methylphenoxy)-2-methyl-butan-3-one of boiling point 108° C./0.5 mbar are obtained.

EXAMPLE 3

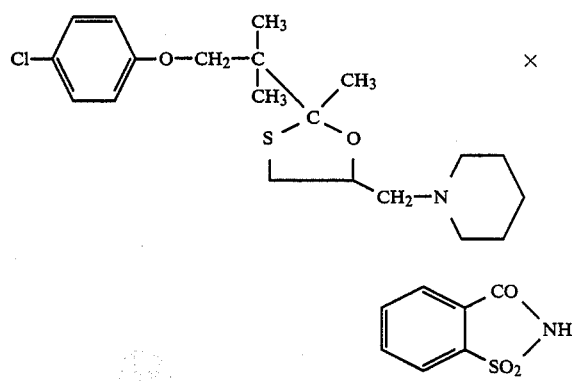

96 g (0.025 mol) of 2-[1-(4-chlorophenoxy)-2-methylprop-2-yl]-2-methyl-5-(piperidin-1-yl-methyl)-1,3-oxathiolane are dissolved in 40 ml of tetrahydrofuran together with 4.6 g (0.025 mol) of saccharine. The solvent is removed in vacuo and the residue is dried under a high vacuum. 14.1 g (98% of theory) of 2-[1-(4-chlorophenoxy)-2-methyl-prop-2-yl]-2-methyl-5-(piperidin-1-yl-methyl)1,3-oxathiolane saccharine salt are obtained as an amorphous substance.

$^1$H-NMR (CDCl$_3$/TMS): δ=4.2–4.4 (m, 1H); 3.6–3.95 (m, 3H) ppm.

PREPARATION OF THE STARTING COMPOUND OF THE FORMULA (II)

3(a)

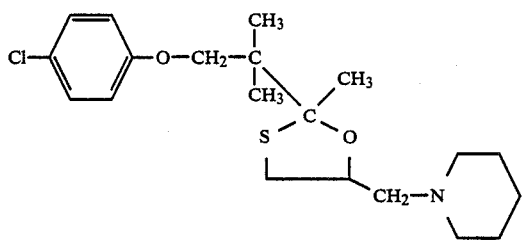

10 g (0.03 mol) of 5-chloromethyl-2-(4-chlorophenoxy)-2-methyl-prop-2-yl]-2-methyl-1,3-oxathiolane and 10 g (0.12 mol) of piperidine are heated at 120° C. for 12 hours. After cooling, the reaction mixture is diluted with ethyl acetate, washed twice with water, dried over sodium sulphate and concentrated in vacuo. The residue is subjected to bulb tube distillation (boiling point: 200° C./0.13 mbar) or is chromatographed over a silica gel column with a mobile phase mixture of petroleum ether/ethyl acetate 2:1.

8 g (69.5% of theory) of 2-[(1-(4-chlorophenoxy)-2-methyl-prop-2-yl]-2-methyl-5-piperidin-1-yl-methyl-1,3-oxathiolane of refractive index $n_D^{20}=1.5440$ are obtained.

PREPARATION OF THE PRECURSOR OF THE FORMULA (III) OF 3A

3(b)

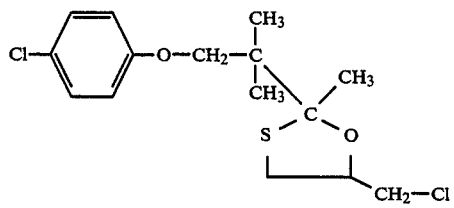

50 g (0.35 mol) of boron trifluoride-etherate are added dropwise to a boiling solution of 80.7 g (0.35 mol) of 4-(4-chlorophenoxy)-3,3-dimethyl-butan-2-one (compare, for example, DE-OS (German Published Specification) No. 3,021,516) and 45 g (0.35 mol) of 1-chloro-3-mercapto-2-propanol in 240 ml of absolute ether. When the addition has ended, the mixture is boiled under reflux for a further 90 minutes. The cooled reaction mixture is washed twice with 100 ml of 0.1 molar sodium bicarbonate solution each time and once with saturated sodium chloride solution, dried over sodium sulphate and freed from the solvent in vacuo. The residue is distilled in vacuo.

50 g (43% of theory) of 5-chloromethyl-2-[1-(4-chlorophenoxy)-2-methyl-prop-2-yl]-2-methyl-1,3-oxathiolane of boiling point 160° C. under 0.3 mbar are obtained.

EXAMPLE 4

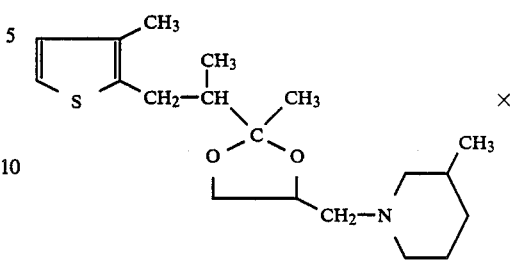

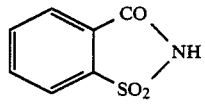

3.3 g (0.01 mol) of 2-methyl-4-(3-methylpiperidin-1-yl-methyl)-2-[1-(3-methylthien-2-yl)-propan-2-yl]dioxolane and 1.8 g (0.01 mol) of saccharine are dissolved together in 50 ml of acetone and the solution is stirred at room temperature for 10 minutes. The solvent is distilled off in vacuo and the residue is triturated with ether and, after decanting, is dried.

4.9 g (96% of theory) of 2-methyl-4-(3-methylpiperidin-1-yl-methyl)-2-[1-(3-methylthien-2-yl)-propan-2-yl]-dioxolane saccharide salt of melting point 39° C.–41° C. are obtained.

PREPARATION OF THE STARTING COMPOUND OF THE FORMULA (II) FOR 4

4(a)

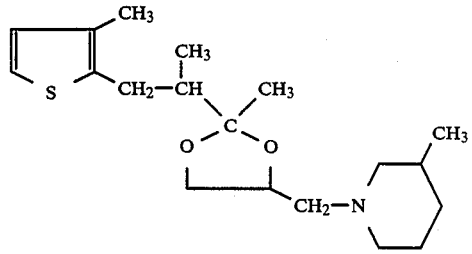

10 g of palladium on charcoal (5 percent) are added to 15 g (0.05 mol) of 2-methyl-4-(3-methylpiperidin-1-yl-methyl)-2-[1-(3-methylthien-2-yl)-propen-2-yl]dioxolane in 150 ml of methanol and hydrogenation is carried out at 80° C. under a pressure of 120 bar for 6 hours. For working up, the catalyst is filtered off and the solvent is removed in vacuo.

14.5 g (96% of theory) of 2-methyl-4-(3-methylpiperidin-1-yl-methyl)-2-[1-(3-methylthien-2-yl)-propan-2-yl]-dioxolane of refractive index $n_D^{20}=1.5139$ are obtained.

PREPARATION OF THE PRECURSOR FOR THE PREPARATION OF 4A

4(b)

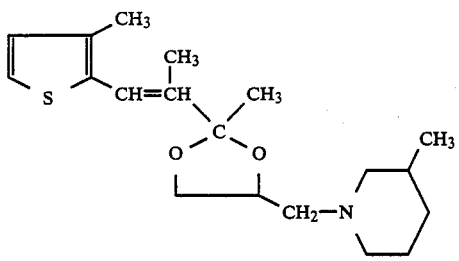

A mixture of 19 g (0.07 mol) of 4-chloromethyl-2-methyl-2-[1-(3-methylthien-2-yl)-propen-2-yl]-dioxolane and 18 g (0.18 mol) of 3-methylpiperidine is heated at 120° C. for 16 hours, with stirring. For working up, the cooled reaction mixture is partitioned between water, and diethyl ether and the organic phase is separated off, dried over magnesium sulphate and evaporated in vacuo. 19 g (81% of theory) of 2-methyl-4-(3-methyl-piperidin-1-yl-methyl)-2-[1-(3-methylthien-2-yl]-propen-2-yl]-dioxolane of refractive index $n_D^{20}$ 1.5402 are obtained.

PREPARATION OF THE STARTING COMPOUND FOR THE PREPARATION OF 4B

4(c)

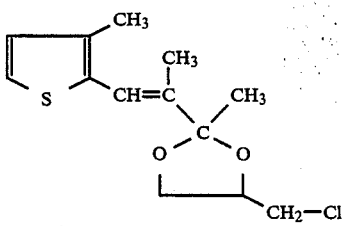

78 g (0.43 mol) of 2-methyl-1-(3-methylthien-2-yl)-buten-3-one and 100 g (0.9 mol) of 3-chloro-propane-1,2-diol in 600 ml of toluene are heated under reflux over a water separator, with the addition of 4 g of acid ion exchanger (Lewasorb A10) for 16 hours. For working up, the cooled reaction mixture is filtered, the filtrate is washed with water and dried over sodium sulphate and the solvent is removed in vacuo.

77 g (65% of theory) of 4-chloromethyl-2-methyl-2-[1-(3-methylthien-2-yl)-propen-2-yl]-dioxolane of refractive index $n_D^{20}$ 1.5430 are obtained.

PREPARATION OF THE STARTING COMPOUND FOR THE PREPARATION OF 4C

4(d)

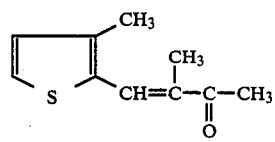

100 ml of a solution of hydrogen chloride in ether (about 9 percent) are added to a mixture of 100 g (0.79 mol) of 3-methyl-thiophene-2-aldehyde and 300 ml of absolute methyl ethyl ketone and the mixture is stirred at room temperature for 24 hours. For working up, the volatile constituents are removed in vacuo and the residue is recrystallized from ether.

82 g (57% of theory) of 2-methyl-1-(3-methylthien-2-yl)-buten-3-one of melting point 72° C. are obtained.

The following saccharine salts of aminomethyl heterocyclic compounds of the general formula (I) are obtained in a corresponding manner and in accordance with the general statements on the preparation:

-continued

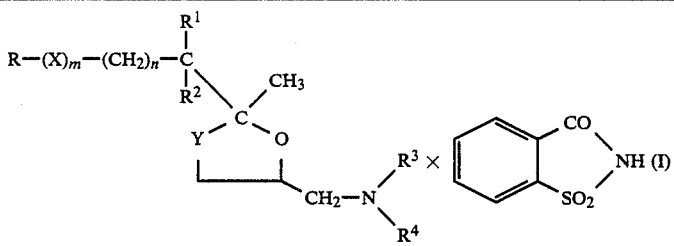

| Ex. No. | R—(X)$_m$—(CH$_2$)$_n$—C(R$^1$)(R$^2$)— | Y | —N(R$^3$)(R$^4$) | 1H—NMR* |
|---|---|---|---|---|
| 7 | 3,4-dichlorophenyl-O-C(CH$_3$)$_2$— | O | 3,3-dimethylpiperidin-1-yl | |
| 8 | 3-(CF$_3$)phenyl-O-C(CH$_3$)$_2$— | O | 3,5-dimethylpiperidin-1-yl | |
| 9 | 3-(CF$_3$)phenyl-O-CH$_2$-C(CH$_3$)$_2$— | O | 3-methylpiperidin-1-yl | 4.5;4.9(m,1H) |
| 10 | 2-methylphenyl-O-CH$_2$-C(CH$_3$)$_2$— | O | piperidin-1-yl | |
| 11 | 4-chloro-3-methylphenyl-O-C(CH$_3$)$_2$— | CH$_2$ | piperidin-1-yl | |
| 12 | 4-chloro-3-ethylphenyl-O-CH$_2$-C(CH$_3$)$_2$— | O | morpholin-4-yl | 4.55;4.81(m,1H); 4.15 (m,4H) |
| 13 | 4-chloro-3-ethylphenyl-O-CH$_2$-C(CH$_3$)$_2$— | O | 2,6-dimethylmorpholin-4-yl | 4.55;4.81(m,1H); 4.1–4.4(m,3H) |
| 14 | 4-chloro-3-ethylphenyl-O-CH$_2$-C(CH$_3$)$_2$— | O | 3-methylpiperidin-1-yl | 4.55;4.85(m,1H); 4.2–4.4(m,1H); 3.4–4.0(m,6H) |

-continued
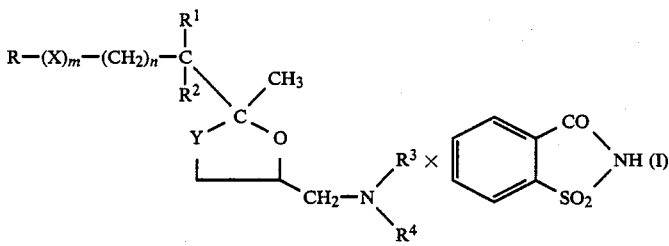
| Ex. No. | R—(X)$_m$—(CH$_2$)$_n$—C(R$^1$)(R$^2$)— | Y | —N(R$^3$)(R$^4$) | 1H—NMR* |
|---|---|---|---|---|
| 15 | 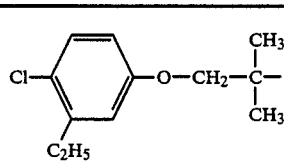 | O | 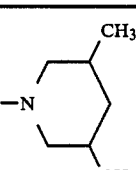 | 4.5;4.8(m,1H); 4.2–4.4(m,1H); 3.4–3.8(m,6H) |
| 16 | 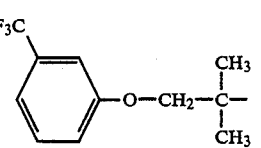 | O | 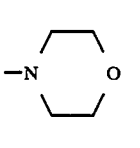 | 4.55;4.851(m,1H); 4.2–4.4(m,1H); 4.1(m,4H) |
| 17 | 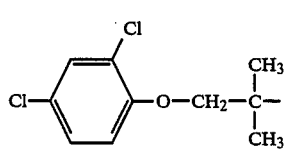 | CH$_2$ | 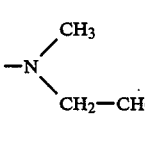 | 4.35;4.55(m,1H); 3.6–3.95(m,6H) |
| 18 | 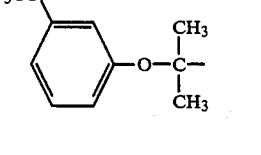 | O | 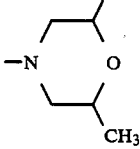 | 4.6–4.9(m,1H); 4.1–4.5(m,4H); 3.4–3.85(m,5H) |
| 19 | 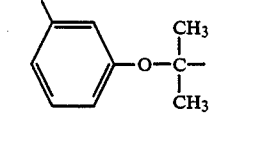 | O | 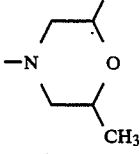 | 4.6–4.9(m,1H); 4.1–4.5(m,1H); 3.4–3.9(m,4H) |
| 20 | 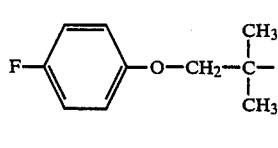 | S | 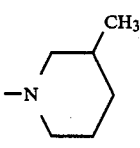 | 4.7–4.9-(m,1H); 3.5–4.0(m,4H) |
| 21 | 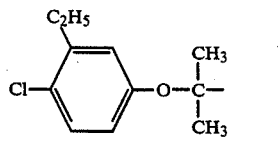 | O | 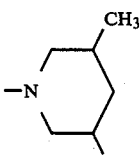 | |

-continued

| Ex. No. | R—(X)$_m$—(CH$_2$)$_n$—C(R$^1$)(R$^2$)— | Y | —N(R$^3$)(R$^4$) | 1H—NMR* |
|---|---|---|---|---|
| 22 | 2-Cl, 4-(F$_3$CO)-C$_6$H$_3$—O—C(CH$_3$)$_2$— | O | 2,6-dimethylmorpholino | 4.7–5.0(m,1H); 4.1–4.5(m,4H) |
| 23 | 3-CH$_3$-C$_6$H$_4$—CH$_2$—C(CH$_3$)$_2$— | CH$_2$ | 2,6-dimethylmorpholino | Mp. 37° C.–42° C. |
| 24 | 3-CH$_3$-C$_6$H$_4$—CH$_2$—C(CH$_3$)$_2$— | CH$_2$ | 3,5-dimethylpiperidino | Mp. 36° C. |
| 25 | 4-F-C$_6$H$_4$—CH$_2$—C(CH$_3$)$_2$— | O | 3,5-dimethylpiperidino | 4.0–5.1(m,2H); 3.25–4.0(m,4H) |
| 26 | C$_6$H$_{11}$—CH$_2$—C(CH$_3$)$_2$— | O | 3,5-dimethylpiperidino | 4.0–4.9(m,2H); 3.1–3.8(m,4H) |
| 27 | 4-Cl-C$_6$H$_4$—CH$_2$—C(CH$_3$)$_2$— | O | 3,5-dimethylpiperidino | 4.1–5.0(m,2H); 3.2–3.8(m,4H) |
| 28 | 2-F-C$_6$H$_4$—CH$_2$—C(CH$_3$)$_2$— | O | 3,5-dimethylpiperidino | 4.1–5.0(m,2H); 3.4–4.0(m,4H) |

-continued

| Ex. No. | R—(X)$_m$—(CH$_2$)$_n$—C(R$^1$)(R$^2$)— | Y | —N(R$^3$)(R$^4$) | 1H—NMR* |
|---|---|---|---|---|
| 29 | 4-F-C$_6$H$_4$—CH$_2$—C(CH$_3$)(CH$_3$)— | O | 3-methylpiperidin-1-yl | 4.1–4.95(m,2H); 3.4–4.0(m,4H) |
| 30 | 3-Cl-C$_6$H$_4$—CH$_2$—C(CH$_3$)(CH$_3$)— | O | 3,5-dimethylpiperidin-1-yl | 4.1–4.95(m,2H); 3.2–3.9(m,4H) |
| 31 | cyclohexyl-CH$_2$—CH(CH$_3$)— | O | 3,5-dimethylpiperidin-1-yl | 4.0–4.8(m,4H); 2.6–3.8(m,8H) |
| 32 | 3-F-C$_6$H$_4$—CH$_2$—C(CH$_3$)(CH$_3$)— | O | 3,5-dimethylpiperidin-1-yl | 4.1–5.0(m,2H); 3.4–4.0(m,4H) |
| 33 | 3-F-C$_6$H$_4$—CH$_2$—C(CH$_3$)(CH$_3$)— | O | 3,5-dimethylpiperidin-1-yl | 3.9'4 5.0(m,3H); 3.2–3.9(m,3H) |
| 34 | cyclohexyl-CH$_2$—C(CH$_3$)(CH$_3$)— | O | 1,4,4-trimethylhexahydroazepin-1-yl | 4.0–4.9(m,2H); 2.5–3.8(m,7H) |
| 35 | 3-CH$_3$-C$_6$H$_4$—CH$_2$—CH(CH$_3$)— | O | 2,6-dimethylmorpholin-4-yl | 4.0–4.9(m,2H); 3.4–3.9(m,4H) |

-continued $$R-(X)_m-(CH_2)_n-\underset{R^2}{\underset{|}{\overset{R^1}{\underset{|}{C}}}}-\underset{\underset{CH_2-N}{\overset{|}{\underset{R^4}{\overset{R^3}{}}}}}{\overset{CH_3}{\underset{Y}{\overset{|}{C}}\diagdown_O}}\cdot\left[\begin{array}{c}\text{benzisothiazole}\\ \text{CO-NH-SO}_2\end{array}\right]\text{(I)}$$

| Ex. No. | $R-(X)_m-(CH_2)_n-\underset{R^2}{\overset{R^1}{C}}-$ | Y | $-N\overset{R^3}{\underset{R^4}{}}$ | 1H—NMR* |
|---|---|---|---|---|
| 36 | 3-methylbenzyl-CH(CH₃)– (m-CH₃-C₆H₄-CH₂-CH(CH₃)–) | O | 3-methylpiperidinyl | 4.2–4.9(M,2H); 3.4–4.0(m,4H) |
| 37 | 4-CH₃-C₆H₄-CH₂-CH(C₂H₅)– | O | piperidinyl | 4.1–4.9(m,2H); 3.4–3.7(m,4H) |
| 38 | 4-CH₃-C₆H₄-CH₂-CH(C₂H₅)– | O | morpholinyl | 3.8–4.9(m,4H); 3.1–3.7(m,4H) |
| 39 | 4-CH₃-C₆H₄-CH₂-CH(C₂H₅)– | O | 3-methylpiperidinyl | 4.1–4.8(m,2H); 3.3–3.7(m,4H) |
| 40 | 4-CH₃-C₆H₄-CH₂-CH(C₂H₅)– | O | 3,5-dimethylpiperidinyl | 4.1–4.8(m,2H); 3.4–3.8(m,4H) |
| 41 | 4-CH₃-C₆H₄-CH₂-CH(C₂H₅)– | O | 2,6-dimethylmorpholinyl | 3.9–4.8(m,3H); 3.4–3.7(m,4H) |
| 42 | 4-CH₃-C₆H₄-CH₂-CH(C₂H₅)– | O | hexamethyleneimino (azepanyl) | 4.1–4.8(m,2H); 3.0–3.7(m,4H) |
| 43 | 3-methylcyclohexyl-CH₂-C(CH₃)₂– | O | 2,6-dimethylmorpholinyl | 4.45;4.8(m,1H); 4.2–4.35(m,3H); 3.4–3.8(m,3H) |

-continued

| Ex. No. | R—(X)$_m$—(CH$_2$)$_n$—C(R$^1$)(R$^2$)— | Y | —N(R$^3$)(R$^4$) | 1H—NMR* |
|---|---|---|---|---|
| 44 | 3-methylcyclohexyl-CH$_2$-C(CH$_3$)$_2$- | O | morpholino | 4.5;4.8(m,1H); 4.05–4.3(m,5H) |
| 45 | 3-methylcyclohexyl-CH$_2$-C(CH$_3$)$_2$- | O | piperidino | 4.5;4.8(m,1H); 4.2–4.3(m,1H); 3.4–3.75(m,4H) |
| 46 | 3-methylcyclohexyl-CH$_2$-C(CH$_3$)$_2$- | O | 3-methylpiperidino | 4.8;4.5(m,H); 4.2–4.4(m,1H); 3.4–3.8(m,4H) |
| 47 | 3-methylcyclohexyl-CH$_2$-C(CH$_3$)$_2$- | O | hexamethyleneimino | 4.8;4.5(m,1H); 4.2–4.35(m,1H); 3.4–3.8(m,4H) |
| 48 | 3-methylcyclohexyl-CH$_2$-C(CH$_3$)$_2$- | O | 3,5-dimethylpiperidino | 4.8;4.5(m,1H); 4.2–4.35(m,1H); 3.4–3.8(m,4H) |
| 49 | 3-methylcyclohexyl-CH$_2$-C(CH$_3$)$_2$- | O | 2,6-dimethylmorpholino | 4.45;4.8(m,1H); 4.2–4.35(m,3H); 3.4–3.8(m,3H) |
| 50 | cyclohexyl-CH$_2$-C(CH$_3$)$_2$- | O | hexamethyleneimino | 4.8;4.5(m,1H); 4.2–4.4(m,1H); 3.4–3.9(m,4H) |
| 51 | 3-fluorophenyl-CH$_2$-C(CH$_3$)$_2$- | O | —N(CH$_3$)(CH$_2$—CH(CH$_3$)$_2$) | |

-continued

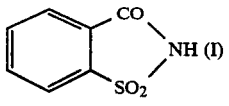

| Ex. No. | R—(X)$_m$—(CH$_2$)$_n$—C(R$^1$)(R$^2$)— | Y | —N(R$^3$)(R$^4$) | 1H—NMR* |
|---|---|---|---|---|
| 52 |  | O | —N(CH$_3$)(CH$_2$—CH(CH$_3$)$_2$) | |
| 53 | 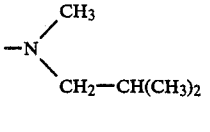 | O | —N(C$_2$H$_5$)((CH$_2$)$_3$—CH$_3$) | |
| 54 |  | O | —N(CH$_3$)(CH$_2$—CH(CH$_3$)$_2$) | |

*The 1H—NMR spectra were recorded in CDCl$_3$ with tetramethylsilane (TMS) as the internal standard. The chemical shift as the δ value ppm is stated.

USE EXAMPLES

The compounds shown below were employed as comparison substances in the following use examples:

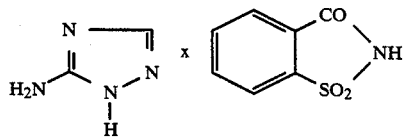
(A)

5-Amino-1,2,4-triazole saccharine salt (known from European Pat. No. 158,074) and

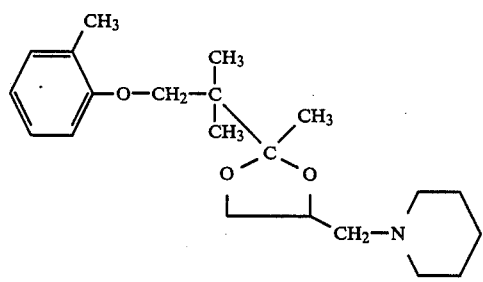
(B)

2-[1-2-Methylphenoxy)-2-methyl-prop-2-yl]-2-methyl-4-(piperidin-1-yl-methyl)-1,3-dioxolane (known from European Pat. No. 97,822).

EXAMPLE A

Erysiphe test (barley)/protective

Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of *Erysiphe graminis* f. sp. hordei.

The plants are placed in a greenhouse at a temperature of about 20° C. and a relative atmospheric humidity of about 80%, in order to promote the development of powdery mildew pustules.

Evaluation is carried out 7 days after the inoculation.

In this test, a clearly superior activity compared with the prior art is shown, for example, by the compounds according to the Preparation Examples 1, 5, 6, 25, 26, 27, 28, 29, 30, 31, 32 and 34.

EXAMPLE B

Pyricularia test (rice)/protective
Solvent: 12.5 parts by weight of acetone.
Emulsifier: 0.3 parts by weight of alkylaryl polyglycol ether.

To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous spore suspension of *Pyricularia oryzae.* The plants are then placed in a greenhouse at 100% relative atmospheric humidity and 25° C.

Evaluation of the disease infestation is carried out 4 days after the inoculation.

In this test, a clearly superior activity compared with the prior art is shown, for example, by the compounds according to the Preparation Examples 2, 7, 8, 13, 14 and 15.

EXAMPLE C

Pyricularia test (rice)/systemic

Solvent: 12.5 parts by weight of acetone

Emulsifier: 0.3 parts by weight of alkylaryl polyglycol ether

To produce a suitable preparation of active compound, 1 part by weight of active compound is mixed with the stated amount of solvent, and the concentrate is diluted with water and the stated amount of emulsifier, to the desired concentration.

To test for systemic properties, standard soil in which young rice plants have been grown is watered with 40 ml of the preparation of active compound. 7 days after the treatment, the plants are inoculated with an aqueous spore suspension of *Pyricularia oryzae.* Thereafter, the plants remain in a greenhouse at a temperature of 25° C. and a relative atmospheric humidity of 100% until they are evaluated.

Evaluation of the disease infestation is carried out 4 days after the inoculation.

In this test, a clearly superior activity compared with the prior art is shown, for example, by the compounds according to the Preparation Examples 2, 7, 8, 10, 13, 14, 15, 25, 26, 27, 28, 33 and 35.

It is understood that the specification and examples are illustrative but not limitative of the present invention and that other embodiments within the spirit and scope of the invention will suggest themselves to those skilled in the art.

We claim:

1. A saccharine salt of an aminomethyl heterocyclic compound of the formula 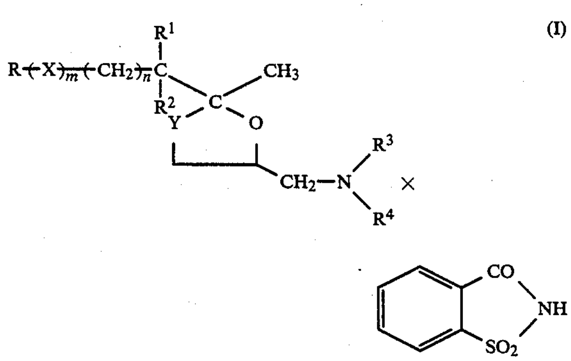 (I)

in which

R represents cycloalkyl or thienyl each optionally substituted by alkyl, or phenyl, or fluoro-, chloro-, alkyl- and/or fluoroalkyl-phenyl, $R^1$ represents hydrogen or alkyl, $R^2$ represents alkyl, $R^3$ and $R^4$, together with the nitrogen atom to which they are bonded, represent a heterocyclic radical of the formula 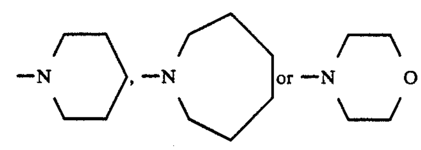 each optionally alkyl substituted, Y represents oxygen, sulphur or the methylene group, m represents 0 or 1 and n represents 0 or 1.

2. A saccharine salt according to claim 1, in which $R^1$ represents hydrogen, or represents straight-chain or branched alkyl with 1 to 4 carbon atoms, and $R^2$ represent straight-chain or branched alkyl with 1 to 4 carbon atoms.

3. A saccharine salt according to claim 1, in which $R^1$ represents hydrogen or methyl, and $R^2$ represents methyl or ethyl.

4. A compound according to claim 1, of the formula

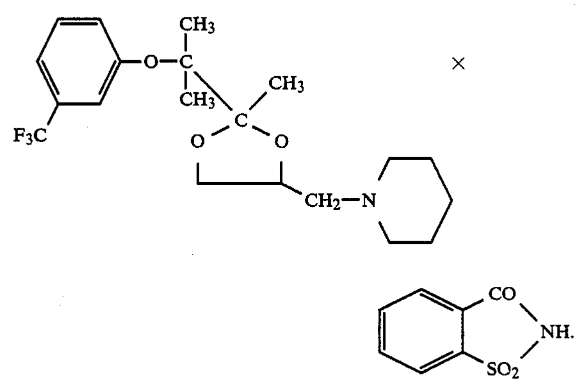

5. A compound according to claim 1, of the formula

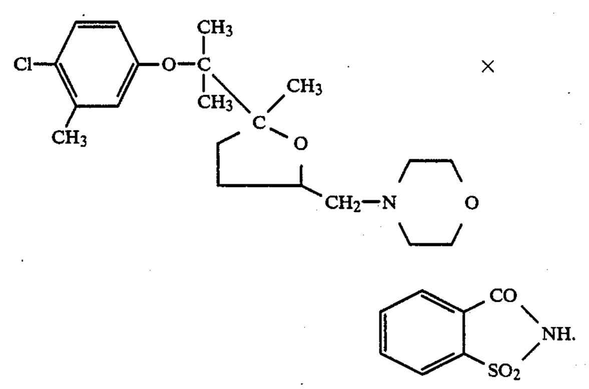

6. A compound according to claim 1, of the formula

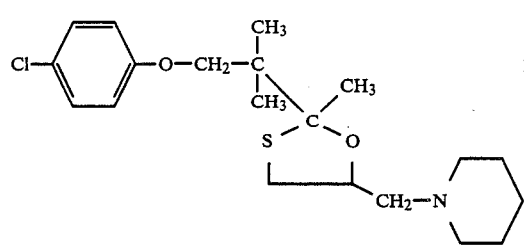 x 5
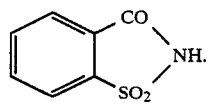
7. A compound according to claim 1, of the formula
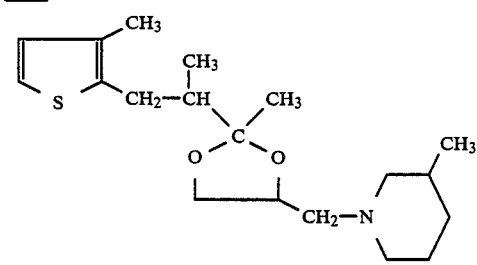 x 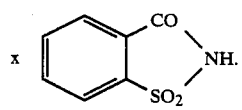
8. A compound according to claim 1, of the formula
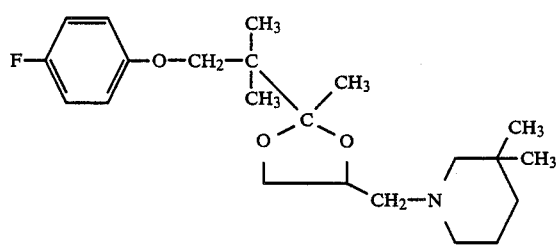 x 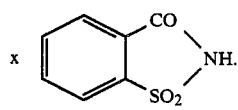
9. A compound according to claim 1, of the formula
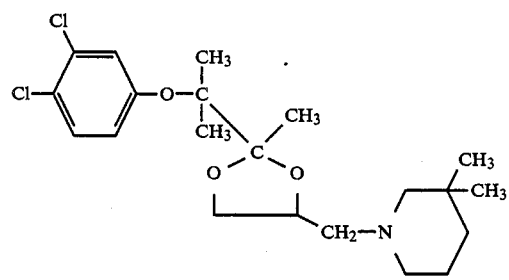 x 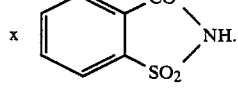
10. A compound according to claim 1, of the formula
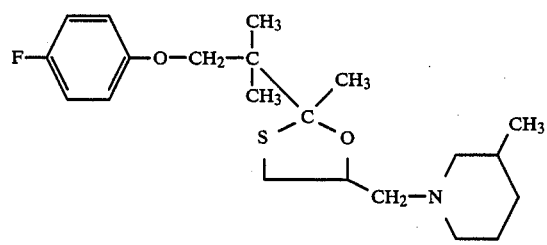 x 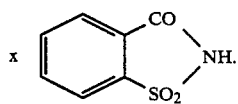
11. A compound according to claim 1, of the formula 12. A compound according to claim 1, of the formula
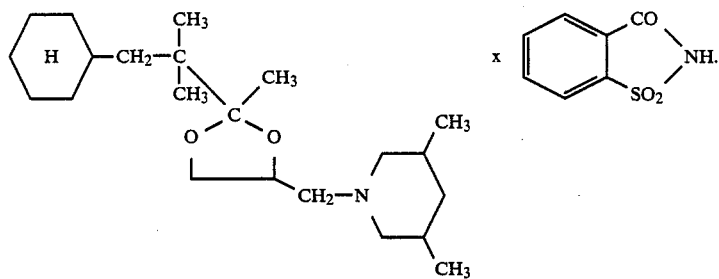
13. A compound according to claim 1, of the formula
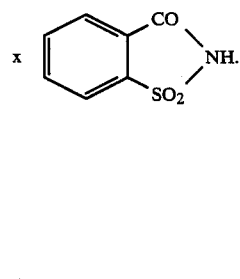
14. A compound according to claim 1, of the formula
15. A compound according to claim 1, of the formula
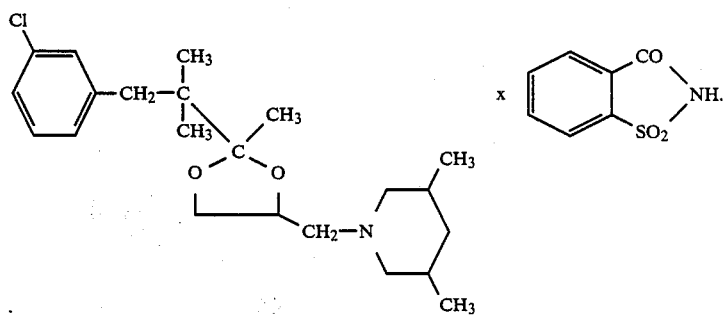
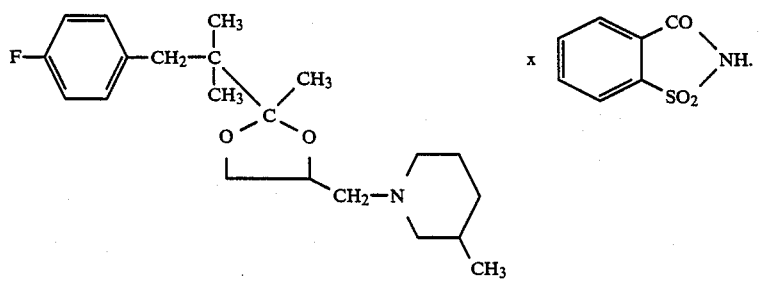

16. A compound according to claim 1, of the formula
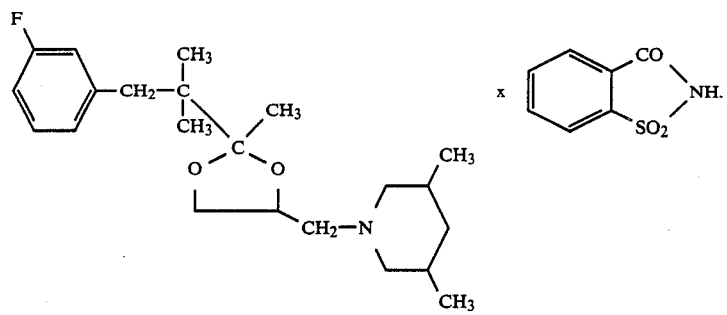
17. A compound according to claim 1, of the formula
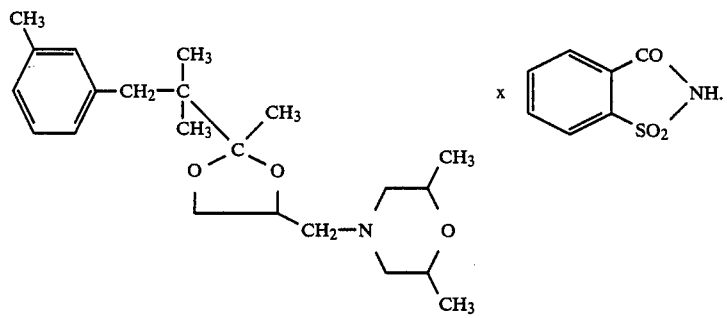
18. A compound according to claim 1, of the formula
19. A compound according to claim 1, of the formula
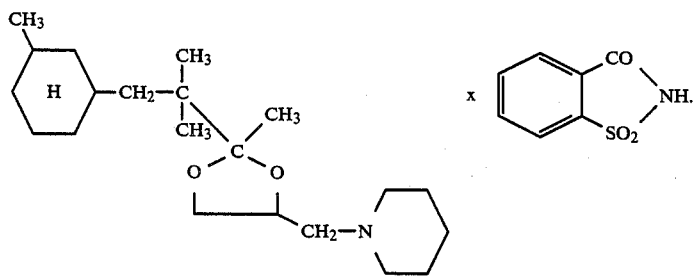

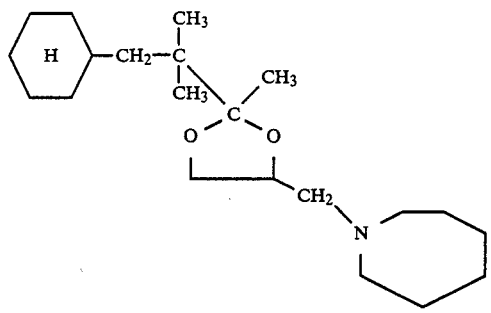 x 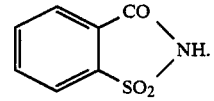
20. A fungicidal composition comprising a fungicidally effective amount of a saccharine salt according to claim 1 and a diluent.
21. A method of combating fungi which comprises applying to such fungi or to a fungus habitat a fungicidally effective amount of a saccharine salt according to claim 1.
* * * * *

UNITED STATES PATENT AND TRADEMARK OFFICE
CERTIFICATE OF CORRECTION

PATENT NO. : 4,826,836

DATED : May 2, 1989

INVENTOR(S) : Joachim Weissmüller, et al

Page 1 of 2

It is certified that error appears in the above-identified patent and that said Letters Patent is hereby corrected as shown below:

| | |
|---|---|
| Col. 1, line 17 | Delete "ylmethyl" and substitute --yl-methyl-- |
| Col. 3, line 13 | Delete "$R^2$" and substitute --$R^1$-- |
| Col. 3, line 25 | After "members" insert --and-- |
| Col. 3, line 27 | Correct spelling of --substituents-- |
| Col. 4, line 18 | Delete "metyl" and substitute --methyl-- |
| Col. 7, line 64 | Correct spelling of --repricipitation-- |
| Col. 7, line 65 | Correct spelling of --amorphous-- |
| Col. 8, lines 11-12 | Correct spelling of --Pythium-- |
| Col. 8, line 57 | Correct --Pyricularia-- |
| Col. 8, line 68 | Before "burning" delete "in" and substitute --with-- |
| Col. 9, line 36 | Delete "orgaic" and substitute --organic-- |
| Col. 9, line 62 | Correct spelling of --compounds-- |
| Col. 10, line 15 | Delete "0.5 and 0.0001%" and substitute --0.5 and 0.001%-- |
| Col. 16, line 32 | Delete "saccharide" and substitute --saccharine-- |
| Col. 17, lines 17-18 | After "water" delete "," |
| Col. 22, Example 16, last column, line 1 | Delete "4.55; 4.851" and substitute --4.55; 4.85-- |
| Col. 22, Example 19, last column, line 2 | Delete "4.1-4.5" and substitute --4.2-4.5-- |
| Col. 24, Example 26, last column line 2 | Delete "3.1-3.8" and substitute --3.2-3.8-- |

UNITED STATES PATENT AND TRADEMARK OFFICE
CERTIFICATE OF CORRECTION

PATENT NO. : 4,826,836

DATED : May 2, 1989

INVENTOR(S) : Joachim Weissmüller, et al

It is certified that error appears in the above-identified patent and that said Letters Patent is hereby corrected as shown below:

Col. 25, Example 33, last column, line 1     Delete "3.945.0" and substitute --3.9-5.0--

Col. 29, Example 49, second column     Delete beginning of formula and substitute

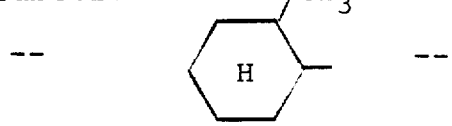

Col. 30, Example 49, last column, line 1     Delete "4.45;4.8" and substitute --4.8;4.5--

Col. 30, Example 49, last column, line 2     Delete "4.2-4.35" and substitute --4.1-4.4--

Col. 33, line 52     Delete "$R-(X)_m-$" and substitute --$R-(O)_m-$--

Signed and Sealed this

Nineteenth Day of June, 1990

Attest:

HARRY F. MANBECK, JR.

Attesting Officer     *Commissioner of Patents and Trademarks*